(12) United States Patent
Jagannathan et al.

(10) Patent No.: US 11,071,763 B2
(45) Date of Patent: Jul. 27, 2021

(54) **METHODS FOR TREATING BENIGN PROSTATIC HYPERTROPHY (BPH) SYMPTOMS USING EXTRACT FROM *AGERATUM* SPP**

(71) Applicant: GE Nutrients, Inc., Irvine, CA (US)

(72) Inventors: V. T. Jagannathan, Chennai (IN); Ramasamy Varadarajan Venkatesh, Hong Kong (CN); Jith Veeravalli, Irvine, CA (US)

(73) Assignee: GE Nutrients, Inc., Irvine, CA (US)

( * ) Notice: Subject to any disclaimer, the term of this patent is extended or adjusted under 35 U.S.C. 154(b) by 0 days.

(21) Appl. No.: 16/456,698

(22) Filed: Jun. 28, 2019

(65) Prior Publication Data
US 2020/0000865 A1 Jan. 2, 2020

Related U.S. Application Data

(60) Provisional application No. 62/692,299, filed on Jun. 29, 2018.

(51) Int. Cl.
*A61K 36/28* (2006.01)
*A61P 13/08* (2006.01)

(52) U.S. Cl.
CPC ........... *A61K 36/28* (2013.01); *A61P 13/08* (2018.01)

(58) Field of Classification Search
None
See application file for complete search history.

(56) References Cited

U.S. PATENT DOCUMENTS

| | | | |
|---|---|---|---|
| 2003/0118661 A1* | 6/2003 | Li | A61K 36/532 424/520 |
| 2005/0084547 A1* | 4/2005 | Subbiah | A61K 36/48 424/740 |

FOREIGN PATENT DOCUMENTS

| | | | |
|---|---|---|---|
| CN | 101623455 | * | 1/2010 |
| CN | 1833030 B | | 7/2014 |
| CN | 106265947 | * | 1/2017 |
| WO | 2005/026375 A2 | | 3/2005 |
| WO | 2006039807 A1 | | 4/2006 |
| WO | 2018/163192 A1 | | 9/2018 |

OTHER PUBLICATIONS

Detering, M., et al., Ageratum Conyzoides L. inhibits 5-alpha-reductase gene expression in human prostate cells and reduces symptoms of benign prostatic hypertrophy in otherwise healthy men in a double blind randomized placebo controlled clinical study; International Union of Biochemistry and Molecular Biology; vol. 43, No. 6, Nov./Dec. 2017, pp. 789-800; Biofactors; DOI 10.1002/biof.1389; Published online Oct. 19, 2017.
Acheampong, F., et al., In vitro Antioxidant and Anticancer Properties of Hydroethanolic Extracts and Fractions of Ageratum conyzoides; EJMP, 7(4): 205-214,2015; Article No. EJMP.2015.083; DOI: 10.9734/EJMP/2015/17088.
Adebayo, A. H., et al., Anticancer and antiradical scavenging activity of Ageratum conyzoides L. (Asteraceae); Pharmacognosy Magazine Jan.-Mar. 2010; 6(21): 62-66; Published online Feb. 13, 2010. doi: 10.4103/0973-1296.59968; 1-13.
Sciarra, A., et al., "Prostate growth and inflammation," Journal of Steroid Biochemistry & Molecular Biology 108 (2008) 254-260.
Robert, G., et al., "Inflammation in benign prostatic hyperplasia: a 282 patients' immunohistochemical analysis," 2009 Prostate December; 69(16): 1774-1780; doi: 10.1002/pros.21027.
Lans, C., "Ethnomedicines used in Trinidad and Tobago for reproductive problems," Journal of Ethnobiology and Ethnomedicine (2007) 3: 13-16; BioMed Central; doi; 10.1186/1746-4269-3-13; Published: Mar. 15, 2007.
Kamboj, A. et al., "Isolation of Stigmasterol and Beta-Sitosterol from petroleum ether extract of aerial parts of Ageratum conyzoides (Asteraceae)," International Journal of Pharmacy and Pharmaceutical Sciences, vol. 3, Issue 1, 2011, 94-96; ISSN-0975-1491.
Kaur, R. et al., "A review on traditional uses, chemical constituents and pharmacology of Ageratum conyzoides L. (Asteraceae)," International Journal of Pharmaceutical & Biological Archives 2014; 5(5); 33-45.
International Searching Authority/U.S., "International Search Report" and "Written Opinion" dated Sep. 9, 2019 in PCT Appln. No. PCT/US2019/039890.

* cited by examiner

*Primary Examiner* — Ralph J Gitomer
(74) *Attorney, Agent, or Firm* — Amin Talati Wasserman LLP; George M. Carrera, Jr.; Valerie Neymeyer-Tynkov

(57) ABSTRACT

An herbal extract and constituents thereof for treatment of BPH and related aging symptoms in males and for addressing male health using extracts from *Ageratum* spp., including, but not limited to, *Ageratum conyzoides*, *Ageratum coeruleum* and *Ageratum houstonianum*, is disclosed herein. At least one compound of plants, and parts of plants, of *Ageratum* spp., such as, but not limited to, N,N-bis(trimethylsilyl)-2-phenyl-7-(trifluoromethyl)quinolon-4-amine, 3',4',5',6',7',8-hexamethoxyflavone, Phytol, Precocene, caryophyllene, squalene, alpha-linolenic acid, (Z,Z)-9,12-octadecadienoic acid, Hexadecanoic acid, Hydrocoumarin, Encecaline-1-(7-methoxy-2,2-dimethyl-2H-chromen-6-yl) ethanone, Senensetin-3,4,5,6,7-pentamethoxy flavone, Beta selinene, Stigmasterol, Beta sitosterol, Quercetin, Quercetin-3-O-rhamnosylglucoside, Linoleic acid, or Conyzorigin can be extracted utilizing a Common Plant Extraction Approach (CPEA). The extraction of compounds can be performed utilizing an ethanol solvent and sterile water solvent and/or ethanol mixed with sterile water (i.e., hydroalcoholic solvents) separately and the concentrated materials obtained as these solvents systems are pooled together (or maintained separately) in order to obtain an herbal extract for the treatment of BPH.

19 Claims, 4 Drawing Sheets

METHODS FOR TREATING BENIGN PROSTATIC HYPERTROPHY (BPH) SYMPTOMS USING EXTRACT FROM *AGERATUM* SPP

This application claims the benefit of U.S. Provisional Application No. 62/692,299, filed Jun. 29, 2018, which is hereby incorporated by reference herein in its entirety.

TECHNICAL FIELD

Embodiments are generally related to field of pharmaceutics, medicine and allied industries. Embodiments are also related to herbal extraction processes and techniques. Embodiments are additionally related to herbal extracts and constituents for treating benign prostate hypertrophy and related aging symptoms. Embodiments are particularly related to process for preparing a novel alleviating Benign Prostatic Hypertrophy (BPH) herbal extract using extract from *Ageratum* spp. (including but not limited to *Ageratum conyzoides*, *Ageratum coeruleum* and *Ageratum houstonianum*) for treatment of Benign Prostate Hypertrophy (BPH).

BACKGROUND

Benign prostatic hyperplasia (BPH) is non-malignant enlargement of the prostate gland. BPH generally begins in a man's thirty's, evolves slowly, and most commonly only causes symptoms after 50. It is common in men age 50 and older with its prevalence being as high as 90% by 85 years of age (American Urological Association Education and Research, Inc., 2003). It may compress the urethra, which courses through the center of the prostate. This can impede the flow of urine from the bladder through the urethra to the outside. It can cause urine to back up in the bladder (retention) leading to the need to urinate frequently during the day and night. Other common symptoms include a slow flow of urine, the need to urinate urgently and difficulty starting the urinary stream. More serious problems include urinary tract infections and complete blockage of the urethra (Lepor, H., "Pathophysiology of benign prostatic hyperplasia in the aging male population," *Rev. Urol.* (2005) 7: S3-S11).

The causes of BPH are not known. One theory is that, as men age, prostate cells accumulate dihydrotestosterone (DHT) produced from testosterone via the enzyme alpha 5 reductase with a concomitant increase in estrogens through increased expression of aromatase which may promote growth factors such as epidermal growth factor and insulin-like growth factor, that lead to enlargement of the prostate. The currently available drugs used for the management of BPH are either a) alpha blockers relax the smooth muscles of the prostate, and the bladder neck, which helps to relieve urinary obstruction caused by an enlarged prostate in BPH, and b) 5-alpha reductase inhibitors block the conversion of the male hormone testosterone into its active form as DHT in the prostate. The prostate enlargement in BPH is thought to be directly dependent on DHT, so these drugs lead to an approximate 25% reduction in prostate size over six to 12 months (Spatafora, S., et al., "Evidence-based guidelines for the treatment of lower urinary tract symptoms related to uncomplicated benign prostatic hyperplasia in Italy: Updated summary from AURO," *Ther. Adv. Urol.* (2012) 4: 279-301).

The most commonly available herbal medicines used in the management of BPH are *Serenoa repensa*, *Pygeum africanum*, *Curcurbita pepo*, *Epilobim* spp., *Hyoxis rooperi*, *Lycopersicum esculentum* (tomato), *Pinus pinaster*, and *Urtica dioico* (Allkanjario, O., and Vitalone, A., "What do we know about phytotherapy of benign Prostatic hyperplasia?" *Life Sci.* (2015) 126: 42-56). A meta-analysis was conducted in 1998 analysing 18 controlled clinical studies showed the therapeutic efficacy of *Serenoa repensa* extracts to be significantly superior to placebo and identical to finasteride (Wilt, T. J., et al. "Saw palmetto extracts for treatment of benign prostatic hyperplasia," *JAMA* (1998) 280: 1604-1609). *Pygeum africanum* is an African herb used in many European prostate health products. It has also been the subject of a large number of separate clinical studies and has been found to stop night time urination and increase the flow of urine during the day (Allkanjari & Vitalone, 2015).

*Ageratum conyzoides* has a long history of use traditionally in Caribbean folk medicines (Lans, C., "Ethnomedicines used in Trinidad and Tobago for reproductive problems," *J. Ethnobiol. Ethnomed.* (2007) 3: 13-16). The use of this species in traditional medicine is also extensive in regions including Brazil. Aqueous extracts of leaves or whole plants have been used to treat colic, colds and fevers, diarrhea, rheumatism, spasms, or as a urinary tonic. While there is little information on this herbal extract to date, it contains a wide variety of chemical compounds including several that may have therapeutic activity including coumarins, sterols (Kamboj, A., and Saluja, A. K., (2011) "Isolation of Stigmasterol and Beta-Sitosterol from petroleum ether extract of aerial parts of *Ageratum conyzoides* (Asteraceae)," *Intl. J. Pharm. Pharm. Sci.* (2011) 3: 94-96.), and flavonoids. In a review of the pharmacological properties of *Ageratum conyzoides*, it was noted that 160 compounds have been identified and the crude fractions have shown multifarious pharmacological activities and were generally found to be safe. (Kaur, R., and Dogra, N. K., "A review on traditional uses, chemical constituents and pharmacology of *Ageratum conyzoides* L. (Asteraceae)," *Intl. J Pharm. Biol. Arch.* (2004) 5: 33-45).

There is limited research on the use of extracts of plants and herbal medicines to improve male heath, particularly to help reduce the symptoms of BPH. There are no citations are literature which discusses use of extracts from *Ageratum conyzoides* for male health and symptoms associated BPH or with the age related decrease in androgens. However, as this extract demonstrates anti-inflammatory activity, anti-spasmodic activity and alpha 5 reductase enzyme inhibition, it is found to be a potential candidate therapy for BPH.

Based on the foregoing a need therefore exists for an improved process for preparing an alleviating Benign Prostatic Hypertrophy (BPH) herbal extract using extract from *Ageratum* spp. (including, but not limited to, *Ageratum conyzoides*, *Ageratum coeruleum* and *Ageratum houstonianum*) for treatment of Benign Prostate Hypertrophy (BPH), as described in greater detail herein.

SUMMARY

The following summary is provided to facilitate an understanding of some of the innovative features unique to the disclosed embodiment and is not intended to be a full description. A full appreciation of the various aspects of the embodiments disclosed herein can be gained by taking the entire specification, claims, drawings, and abstract as a whole.

It is, therefore, one aspect of the disclosed embodiments to provide for an improved herbal extract for treatment of Benign Prostatic Hypertrophy (BPH).

It is another aspect of the disclosed embodiments to provide for an improved process for preparing herbal extract for the treatment of Benign Prostatic Hypertrophy (BPH).

In one embodiment, a method for treating symptoms associated with benign prostatic hyperplasia in a human male subject is described, comprising administering to the subject in need of such treatment an effective amount of a composition comprising *Ageratum* spp. wherein the symptoms are decreased. Symptoms may include urinary frequency, urinary urgency, inflammation, urethra/urinary tract obstruction, and urinary tract infection.

In another embodiment, the composition can be used to inhibit 5-alpha-reductase activity, in particular, inhibition of 5-alpha-reductase type 2 activity.

It is further aspect of the disclosed embodiments to provide for an improved process for preparing a novel herbal extract using the aerial vegetative biomass (stem, leaf) of *Ageratum conyzoides* and its associated species for the treatment of Benign Prostatic Hypertrophy (BPH).

The aforementioned aspects and other objectives and advantages can now be achieved as described herein. An herbal extract and constituents thereof for treatment of BPH and related aging symptoms in males and for addressing male health using extracts from *Ageratum* spp., including but not limited to *Ageratum conyzoides, Ageratum coeruleum* and *Ageratum houstonianum*, is disclosed herein. At least one compound of plants, *Ageratum* spp., such as, but not limited to, N,N-bis(trimethylsilyl)-2-phenyl-7-(trifluoromethyl)quinolon-4-amine, 3',4',5',6',7',8-hexamethoxyflavone, Phytol, Precocene, caryophyllene, squalene, alpha-linolenic acid, (Z,Z)-9,12-octadecadienoic acid, Hexadecanoic acid, Hydrocoumarin, Encecaline-1-(7-methoxy-2,2-dimethyl-2H-chromen-6-yl)ethanone, Senensetin-3,4,5,6,7-pentamethoxy flavone, Beta selinene, Stigmasterol, Beta sitosterol, Quercetin, Quercetin-3-O-rhamnosylglucoside, Linoleic acid, or Conyzorigin can be extracted utilizing a Common Plant Extraction Approach (CPEA). The extraction of compounds can be performed utilizing an ethanol solvent and sterile water solvent and/or ethanol mixed with sterile water (i.e., hydro-alcoholic solvents) separately and the concentrated materials obtained as these solvents systems are pooled together (or maintained separately) in order to obtain an herbal extract for the treatment of BPH. Other hydro-alcoholic mixtures are contemplated, for example, methanol-water, and the like.

The common Plant Extraction Approach (CPEA) described herein can be a principle extraction technique that is well known in the art for extracting the compounds of a plant. Initially, the aerial vegetative biomass of *Ageratum* spp. (preferably 60 to 90 day old plants) can be sliced into pieces (approx. 1 inch length or square in size) and dried at open sunlight (3-4 hours) for the removal of the moisture or water content attached with the aerial biomass, and subsequently shade dried at room temperature. The sliced pieces can be also dried using a fluid flash dryer. Further, a mechanized pulverizing machine can be employed to grind the dried plant slices into coarse powder in order to thereby extract the compounds using the ethanol and sterile water, and/or ethanol mixed with sterile water solvents separately. The solvent extraction process described herein can be performed at a 1:10 (W/V) ratio using a Soxhlet apparatus for ethanol extraction and sterile water extraction separately and/or mixing of ethanol and water extraction, followed by removal of solvents from the extracts using a rotary evaporator under reduced pressure.

The compounds obtained at both the ethanol solvent extraction process and the sterile water solvent extraction process, and/or mixing of ethanol and water extraction processes are further pooled together (or used separately) in order to form the herbal extract for treating the BPH and its related aging issues in male subjects. These exemplary extraction steps may be performed in any effective order, and can be varied, repeated, adjusted, or otherwise intercombined with other processing steps.

The compounds extracted at the aqueous and hydro-alcoholic extraction process can include compounds such as, for example, but not limited to, Quercetin-3-O-rhamnopyranoside, quercetin-3,7-diglucopyranoside, p-Hydroxybenzoic acid, N,N-bis(trimethylsilyl)-2-phenyl-7-(trifluoromethyl)quinolon-4-amine, 1-deoxy-D-mannitol, 15-hydroxypentadecanoic acid, 2-chromenone, 3',4',5',6',7',8-hexamethoxyflavone, 3,5-di-tert-butylbenzoic acid, 3-phenylisoquinoline, 3,7,11,15-tetramethylhexadec-2-en-1-ol, 4-tert-butyl-2,6-dimethylacetophenone, 6-vinyl-7-methoxy-2,2-dimethylchromene, Anhydro-D-mannosan, beta-Funebrene, caryophyllene, coumarin, hexa-O-methyl-myricitin, hydrocoumarin, linoleoyl chloride, methyl cis-11, 14,17-icosatrienoate, methyl linoleate, Neophytadiene, p-Octylacetophenone, 2,4,6-tris(1,1-dimethylethyl)phenol, phytol, precocene I and II, squalene, and beta sitosterol.

The compounds extracted at the ethanol solvent extraction process can include compounds such as, for example, but not limited to, N,N-bis(trimethylsilyl)-2-phenyl-7-(trifluoromethyl)quinolon-4-amine, (Z)-Beta-farnesene, 1-(3,5-di-tert-butyl-4-hydroxyphenyl)ethanone, 2-(1,3-benzodioxol-5-yl)-5-hydroxy-3,6,7,8-tetramethoxy-4H-chromen-4-one, 2-(3,4-dimethoxyphenyl)-5,6,7,8-tetramethoxy-4H-1-benzopyran-4-one, 2,4,6-tri-tert-butylphenol, 2-chromanone, 2H-chromen-2-one, 3',4',5,6,7,8-hexamethoxyflavone, 3,5-di-tert-butylbenzoic acid, 3,7,11,15-tetramethylhexadec-2-en-1-ol, 3-thujanol, 4-tert-butyl-2,6-dimethylacetophenone, 6-demethoxyageratochromene, 6-vinyl-7-methoxy-2,2-dimethylchromene, (Z,Z)-9,12-octadecadienoic acid, all-trans-squalene, alpha-benzopyrone, alpha-caryophyllene, alpha-linolenic acid, alpha tocopherol-beta-D-mannoside, beta-sesquiphellandrene, hexyl [4-(2-phenylpropan-2-yl)phenyl] butylphosphonate, Caryophyllene, Coumarin, Delta-cadinene, Dotriacontane, Hexadecanoic acid, hydrocoumarin, methyl cis-11,14,17-icosatrienoate, methyl linoleate, methyl palmitate, neophytadiene, n-hexatriacontane, n-tetracontane, n-tetracosane, n-tetratriacontane, n-triacontane, Phytol, precocene I, Precocene II, squalene, stigmasterol, Stigmasta-4,22-dien-3beta-ol, and Tetracontane. The solvents utilized for extracting compound herein should not be construed in any limiting sense. Those skilled in the art can understand that similar types of solvents such as hexane, ethyl acetate, acetone, chloroform, dichloromethane, etc. can also tried for preparing herbal extraction and developing the formulation for the treatment of BPH.

DETAILED DESCRIPTION

Figure 1A:
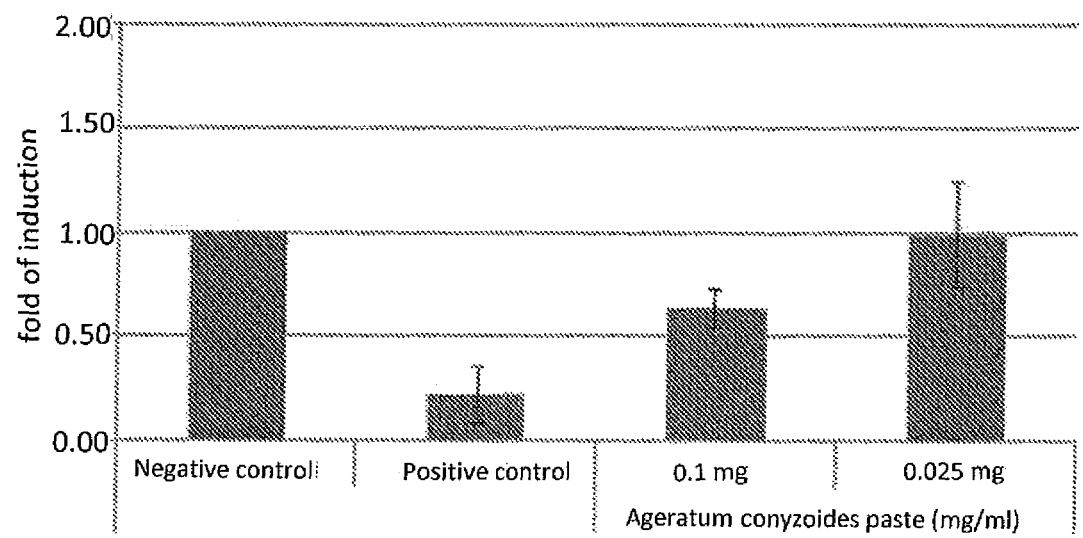
FIG. 1A depicts the results of gene expression profiles in human prostate cells of 5-alpha-reductase type 1 after 48 hours of cell exposure to *A. conyzoides* paste in accordance with an embodiment of the of the present invention.

The particular values and configurations discussed in these non-limiting examples can be varied and are cited merely to illustrate at least one embodiment and are not intended to limit the scope thereof.

The embodiments now will be described more fully hereinafter with reference to the accompanying drawings, in which illustrative embodiments of the invention are shown. The embodiments disclosed herein can be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. As used herein, the term "and/or" includes any and all combinations of one or more of the associated listed items.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In the present disclosure, the terms benign prostatic hypertrophy (BPH) is considered to be generally synonymous with the modern term benign prostatic hyperplasia (BPH).

An herbal extract and constituents thereof for treatment of BPH and related aging symptoms in males and for addressing male health using extracts from *Ageratum* spp., including but not limited to *Ageratum conyzoides*, *Ageratum coeruleum* and *Ageratum houstonianum*, is disclosed herein. At least one compound of plants, *Ageratum* spp., such as, but not limited to, N,N-bis(trimethylsilyl)-2-phenyl-7-(trifluoromethyl)quinolon-4-amine, 3',4',5',6',7',8-hexamethoxyflavone, Phytol, Precocene, caryophyllene, squalene, alpha-linolenic acid, (Z,Z)-9,12-octadecadienoic acid, Hexadecanoic acid, Hydrocoumarin, Encecaline-1-(7-methoxy-2,2-dimethyl-2H-chromen-6-yl)ethanone, Senensetin-3,4,5,6,7-pentamethoxy flavone, Beta selinene, Stigmasterol, Beta sitosterol, Quercetin, Quercetin-3-O-rhamnosylglucoside, Linoleic acid, or Conyzorigin can be extracted utilizing a Common Plant Extraction Approach (CPEA). The extraction of compounds can be performed utilizing an ethanol solvent and sterile water solvent and/or ethanol mixed with sterile water (i.e., hydro-alcoholic solvents) separately and the concentrated materials obtained as these solvents systems are pooled together (or maintained separately) in order to obtain an herbal extract for the treatment of BPH. Other hydro-alcoholic mixtures are contemplated, for example, methanol-water, and the like.

The common Plant Extraction Approach (CPEA) described herein can be a principle extraction technique that is well known in the art for extracting the compounds of a plant. Initially, the aerial vegetative biomass of *Ageratum* spp. (preferably 60 to 90 day old plants) can be sliced into pieces (approx. 1 inch length or square in size) and dried at open sunlight (3-4 hours) for the removal of the moisture or water content attached with the aerial biomass, and subsequently shade dried at room temperature. The sliced pieces can be also dried using a fluid flash dryer. Further, a mechanized pulverizing machine can be employed to grind the dried plant slices into coarse powder in order to thereby extract the compounds using the ethanol and sterile water, and/or ethanol mixed with sterile water solvents separately. The solvent extraction process described herein can be performed at a 1:10 (W/V) ratio using a Soxhlet apparatus for ethanol extraction and sterile water extraction separately and/or mixing of ethanol and water extraction, followed by removal of solvents from the extracts using a rotary evaporator under reduced pressure.

The compounds obtained at both the ethanol solvent extraction process and the sterile water solvent extraction process, and/or mixing of ethanol and water extraction processes are further pooled together (or used separately) in order to form the herbal extract for treating the BPH and its related aging issues in male subjects. These exemplary extraction steps may be performed in any effective order, and can be varied, repeated, adjusted, or otherwise intercombined with other processing steps.

The compounds extracted at the aqueous and hydro-alcoholic extraction process can include compounds such as, for example, but not limited to, Quercetin-3-O-rhamnopyranoside, quercetin-3,7-diglucopyranoside, p-Hydroxybenzoic acid, N,N-bis(trimethylsilyl)-2-phenyl-7-(trifluoromethyl)quinolon-4-amine, 1-deoxy-D-mannitol, 15-hydroxypentadecanoic acid, 2-chromenone, 3',4',5',6',7',8-hexamethoxyflavone, 3,5-di-tert-butylbenzoic acid, 3-phenylisoquinoline, 3,7,11,15-tetramethylhexadec-2-en-1-ol, 4-tert-butyl-2,6-dimethylacetophenone, 6-vinyl-7-methoxy-2,2-dimethylchromene, Anhydro-D-mannosan, beta-Funebrene, caryophyllene, coumarin, hexa-O-methylmyricitin, hydrocoumarin, linoleoyl chloride, methyl cis-11, 14,17-icosatrienoate, methyl linoleate, Neophytadiene, p-Octylacetophenone, 2,4,6-tris(1,1-dimethylethyl)phenol, phytol, precocene I and II, squalene, and beta sitosterol.

The compounds extracted at the ethanol solvent extraction process can include compounds such as, for example, but not limited to, N,N-bis(trimethylsilyl)-2-phenyl-7-(trifluoromethyl)quinolon-4-amine, (Z)-Beta-farnesene, 1-(3,5-di-tert-butyl-4-hydroxyphenyl)ethanone, 2-(1,3-benzodioxol-5-yl)-5-hydroxy-3,6,7,8-tetramethoxy-4H-chromen-4-one, 2-(3,4-dimethoxyphenyl)-5,6,7,8-tetramethoxy-4H-1-benzopyran-4-one, 2,4,6-tri-tert-butylphenol, 2-chromanone, 2H-chromen-2-one, 3',4',5,6,7,8-hexamethoxyflavone, 3,5-di-tert-butylbenzoic acid, 3,7,11,15-tetramethylhexadec-2-en-1-ol, 3-thujanol, 4-tert-butyl-2,6-dimethylacetophenone, 6-demethoxyageratochromene, 6-vinyl-7-methoxy-2,2-dimethylchromene, (Z,Z)-9,12-octadecadienoic acid, all-trans-squalene, alpha-benzopyrone, alpha-caryophyllene, alpha-linolenic acid, alpha tocopherol-beta-D-mannoside, beta-sesquiphellandrene, hexyl [4-(2-phenylpropan-2-yl)phenyl] butylphosphonate, Caryophyllene, Coumarin, Delta-cadinene, Dotriacontane, Hexadecanoic acid, hydrocoumarin, methyl cis-11,14,17-icosatrienoate, methyl linoleate, methyl palmitate, neophytadiene, n-hexatriacontane, n-tetracontane, n-tetracosane, n-tetratriacontane, n-triacontane, Phytol, precocene I, Precocene II, squalene, stigmasterol, Stigmasta-4,22-dien-3beta-ol, and Tetracontane. The solvents utilized for extracting compound herein should not be construed in any limiting sense. Those skilled in the art can understand that similar types of solvents such as hexane, ethyl acetate, acetone, chloroform, dichloromethane, etc. can also tried for preparing herbal extraction and developing the formulation for the treatment of BPH.

The solvents utilized for extracting compound herein should not be construed in any limiting sense. Those skilled in the art can understand that similar types of solvents such as hexane, ethyl acetate, acetone, chloroform, dichloromethane, and the like, can also tried for preparing herbal extraction and developing the formulation for the treatment of BPH.

The in vitro evaluation of activity modulation of 5-alpha-reductase type 1 and type 2 gene expression profiles on human prostate cells was performed as follows.

Gene Expression Study

The study measured 5-alpha-reductase gene type 1 and type 2 expression by real time polymerase chain reaction (qRT-PCR) after 48 h of treatment with *Ageratum conyzoides* (*A. conyzoides*) in human prostate epithelial cells.

*A. conyzoides* samples were made from an ethyl alcohol extract powder of the aerial parts of *A. conyzoides* available from Gencor Pacific, Hong Kong. The reference positive control was *Serenoa repens* (*S. repens*), available from Euromed (Barcelona, Spain), a pharmacologically active compound used to treat prostate hyperplasia.

The human prostate epithelial cells (PNT1A: human postpubertal prostate cells, source ECACC 95012614) were solubilized directly into the culture medium at 0.1 and 0.025 mg/mL in RPMI medium, 10% fetal calf serum, 2 mmol/L L-glutamine, 1.0 mmol/L sodium pyruvate, 4.5 g/L glucose containing 100 µg/mL streptomycin and 100 U penicillin.

Cells were seeded in 6-well plates for 24 h at 14,000 cells/well and cultures were treated for 24 h with 10 ng/ml testosterone. Fresh medium was added, supplemented with test products at 0.1/mL and 0.025 mg/mL. Untreated cells were used as negative controls and cells treated with 10 mg/mL of *S. repens* were used as positive control. Every sample was tested in duplicate. After 48 h of exposure, total RNA was purified from cells using the TriAZol protocol according to the manufactures instructions (Trizol-Invitrogen).

Total RNA was extracted using a guanidine thiocyanate-based reagent according to the manufactures instructions (Trizol-Invitrogen). After precipitation and centrifugation, RNA was resuspended in 20 mL of sterilized water and its concentration determined spectrophotometrically, with 300 mg of total RNA retro-transcribed into cDNA using random primers at 37° C. for 2 h in a thermal cycler following manufacturer's instruction (Applied Byosystems, Foster City, Calif.).

Changes in gene expression were analyzed by reverse transcription (RT-(PCR)) technology using Syber-green based chemistry (R. Higuchi, et al., "Kinetic PCR analysis: real-time monitoring of DNA amplification reactions," *Biotechnology* (NY) (1993) 11:1026-1030). Primer pair sequences for tyrosinase analysis were designed across intron-exon spanning regions and blasted again nonredundant database (Genebank) to verify the unicity of amplified region across the genome. This signal increases in direct proportion to the amount of PCR product in a reaction. By recoding the amount of fluorescence emission at each cycle, it is possible to monitor the PCR reaction during exponential phase where the first significant increase in the amount of PCR product correlated to the initial amount of target template. Changes in gene expression profile were measured using the comparative Ct (cycle threshold) method, with 28S ribosomal RNA used as reference control for data normalization. If the reduction is two times lower compared with the negative control (i.e., fold of reduction >2), the sample is considered effective in reducing the enzyme expression, and thereby inhibits enzyme activity.

In vitro methods of study are interesting alternative systems when compared to traditional in vivo tests in order to evaluate biological properties of ingredients or finished products for biomedical use. The aim of the present study is to find out and quantify the changing in the expression level of 5-alpha-reductase in human prostate cells. This enzyme is also expressed in skin melanocytes, fibroblasts and keratinocytes and transforms testosterone into dihydrotestosterone, a key metabolite implicated in various biological functioning. After birth the 5-alpha-reductase (type1) is expressed in more locations, including the liver, skin, scalp and prostate. 5-alpha-reductase (type 2) is expressed in prostate, seminal vesicles, epididymis, liver, and to a lesser extent the scalp and skin.

In this in vitro test fibroblasts are pre-treated with testosterone in order to induce the production of 5-alpha-reductase and are exposed subsequently to the various test substances for 48 hours. A titrated extract of *Serenoa repens* (Saw palmetto), a well known pharmacologically active compound used to treat the prostate hyperplasia is used as a positive control.

For example, an in vitro study on the evaluation of activity modulation of 5 alpha reductase type 1 gene expression profiles on human prostate cells using the extract of *Ageratum* spp. was conducted. After 48 hours exposure the sample showed a slight ability to reduce the expression of 5-alpha-reductase compared to the untreated control but only at the higher concentration (0.1 mg/ml). The sample showed a 1.6 times reduction in the 5-alpha-reductase expression compared to untreated control, whose level has been arbitrary settled as 1. See, FIG. 1A.

The *Ageratum conyzoides* extract (paste) showed an $IC_{50}$ (concentration that showed 50% cell mortality) of 0.23 mg/ml. The concentrations used in the in vitro examples were 0.1 mg/ml and 0.025 mg/ml.

TABLE 1

| Sample | 5-alpha-reductase type 1 expression (DS) | Fold of reduction compared to Negative control |
|---|---|---|
| *Ageratum conyzoides* paste Batch: NC/HGP/13001 0.1 mg/ml | 0.63 (±0.10) | 1.6 (slight reduction) |
| *Ageratum conyzoides* paste Batch: NC/HGP/13001 0.025 mg/ml | 0.99 (±0.25) | 1.0 (no reduction) |

TABLE 1-continued

| Sample | 5-alpha-reductase type 1 expression (DS) | Fold of reduction compared to Negative control |
|---|---|---|
| Serenoa repens Euromed Batch 065031 10 µg/ml (Positive control) | 0.22 (±0.13) | 4.5 |
| Negative control | | 1 |

As shown in Table 1 and FIG. 1A, after 48 hours exposure the sample shows a slight ability to reduce the expression of 5-alpha-reductase type 1 compared to the untreated control but only at the higher concentration (0.1 mg/ml). The sample shows a 1.6 times reduction in the 5-alpha-reductase expression compared to untreated control, whose level has been arbitrary settled as 1.

Yet another in vitro study on the evaluation of activity modulation of 5 alpha reductase type 2 gene expression profiles on human prostate cells using the extract of *Ageratum* spp. was conducted. The extract produced a significant reduction (2.6 times) of the activity of the enzyme demonstrating the efficacy of the herbal extract of *ageratum* spp. in reducing the symptoms of BPH. See, FIG. 1B.

TABLE 2

| Sample | 5-alpha-reductase type 2 expression (DS) | Fold of reduction compared to Negative control |
|---|---|---|
| Ageratum conyzoides paste Batch: NC/HGP/13001 0.1 mg/ml | 0.38 (±0.06) | 2.6 (good reduction) |
| Ageratum conyzoides paste Batch: NC/HGP/13001 0.025 mg/ml | 1.11 (±0.41) | <1 (no reduction) |
| Serenoa repens Euromed Batch 065031 10 µg/ml (Positive control) | 0.03 (±0.02) | 33.3 |
| Negative control | | 1 |

Figure 1B:
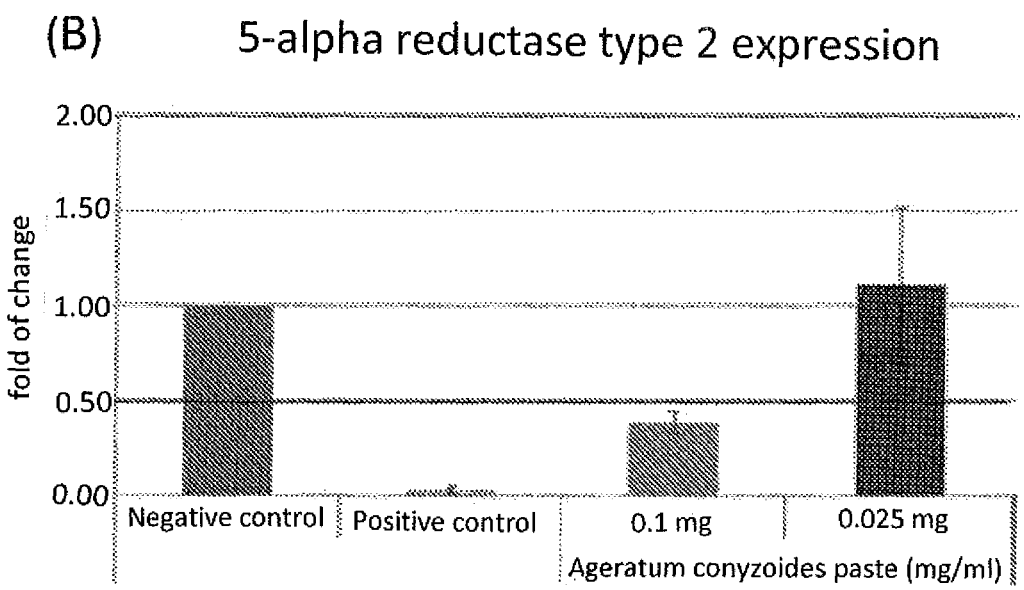
FIG. 1B depicts the results of gene expression profiles in human prostate cells of 5-alpha-reductase type 2 after 48 hours of cell exposure to *A. conyzoides* paste in accordance with an embodiment of the of the present invention.

As shown in Table 2 and FIG. 1B, after 48 hours exposure the sample is effective in reducing the expression of 5-alpha-reductase type 2 compared to the untreated control in a dose dependent way. The highest effect is pointed out at 0.1 mg/ml concentration. The sample shows a 2.6 times reduction of the 5-alpha-reductase type 2 expression compared to untreated control, whose level has been arbitrary settled as 1.

In summary, the gene expression of 5-alpha-reductase types 1 and 2 was evaluated after 48 h of cell exposure to *A. conyzoides*. The negative control level was set at a value of 1.0. The positive control, *S. repens* showed a reduction of 5-alpha-reductase enzyme type 1 (from 1.0 to 0.22, SD 0.13) and 5-alpha-reductase enzyme type 2 (from 1.0 to 0.03, SD 0.02) relative to negative control. Treatment with *A. conyzoides* was effective in reducing the expression of mRNA coding for the enzyme 5-alpha-reductase type 2 in human prostate cells compared with untreated cells from 1.0 to 0.38±0.06 (2.6 times reduction) at a concentration of 0.1 mg/ml. In addition, *A. conyzoides* showed a partial activity in inhibiting 5-alpha-reductase type 1 enzyme (from 1.0 to 0.63, SD 0.1) (or 1.6 times). There was no change in type 1 or type 2 enzyme activity at 0.025 mg/ml of *A. conyzoides* (FIGS. 1A, 1B).

Clinical Study

A clinical trial was conducted with the herbal extract of *Ageratum* spp. on the human prostate cells for a short duration of 12 weeks period in Brisbane, Australia. The trial assessed efficacy of the herbal extract made out of *Ageratum* spp. on the symptoms of BPH, associated aging-related symptoms and changes in PSA levels, sex hormones, lipids and blood sugar levels in middle aged and older males. *Ageratum* spp. Extract was found to be very successful in treating BPH and related symptoms.

The Clinical trial conducted with the herbal extract of *Ageratum* spp. on the prostate cells was registered with the Australian New Zealand Clinical Trials Registry (ANZCTR) with Trial ID. ACTRN No: 12614001074684. The study was carried out according to the principles expressed in the Declaration of Helsinki and was approved by the Queensland Clinical Trial Network Human Research Ethics Committee (QCTN) No: 2014001.

The clinical trial was published in a research communication entitled "*Ageratum conyzoides* L. inhibits 5-alpha-reductase gene expression in human prostate cells and reduces symptoms of benign prostatic hypertrophy in otherwise healthy men in a double blind randomized placebo controlled clinical study," Biofactors November/December (2017) 43 (6): 789-800, which is incorporated by reference in its entirety.

Specifically, this was a single-site, double-blind, randomized, short-duration (12 weeks) clinical trial utilizing active and placebo arms to assess the efficacy and safety of *A. conyzoides* extract, assessing the symptoms of BPH, steroid metabolism, prostate specific antigen (PSA), lipids and blood glucose levels and associated aging-related symptoms in middle aged and older men.

The investigational composition was a small capsule shaped red-brown colored film coated tablet containing 250 mg of a powdered ethyl alcohol extract of the aerial parts of *A. conyzoides*. The placebo tablet was identical in size and appearance (also red-brown colored film coated) containing maltodextrin. The products were supplied to the researchers by Gencor Pacific, Hong Kong.

Useful dosages of *Ageratum* spp. extracts can be 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, or 1000 mg. The dosage can be administered orally once per day. In a preferred dosage, *A. conyzoides* extract can be administered in amounts of 50 mg, 100 mg, 150 mg, 200 mg, 250 mg, 300 mg, 350 mg, 400 mg, 450 mg, or 500 mg once daily, orally.

The dietary supplement can be provided in effective dosages from about 0.5 mg/kg to about 5.0 mg/kg, on a daily basis to a human male subject. In one embodiment, the dietary supplement can be provided in effective dosages from about 2.5 mg/kg to about 3.5 mg/kg, on a daily basis to a human male subject.

In the clinical trial the efficacy of the herbal extract of *Ageratum* spp. was assessed mainly for the primary symptoms of Benign Prostatic Hypertrophy (BPH) using the International Prostate Symptom Score (IPSS), which includes assessment of the quality of life. The secondary outcome of measurement on aging related symptoms using the Aging Male Symptoms (AMS) questionnaire including questions on psychological, somatic and sexual indicators. In both the cases the subjects were completed on the questionnaires of pre-trial (baseline data) and data on 4, 8, and 12 weeks. See, FIG. 2.

Daily day- and night-time urinary frequency was also assessed using a 7-day diary at baseline (for 7 days prior to commencement of treatment), and again at 4-, 8-, and at 12-weeks.

Participants were randomly allocated (blinded) to the active or placebo group and were instructed to take a single tablet (q.d.) with the evening meal for 12 weeks.

Initially, 106 men were enrolled and commenced treatment in the study, with 98 completing the study; 52 in the active treatment group and 46 in the placebo group. There were eight withdrawals from the study; three from active treatment group; five from placebo group. There were no significant differences between the active treatment and placebo groups for average age, anthropometric measures and the lifestyle factors. The sex hormone profiles were similar between both groups, as was total cholesterol, triglycerides and blood glucose levels. The study cohort had normal full blood count, renal and liver function parameters. The average PSA levels were similar in both groups at baseline as a total cohort and also when stratified for age, (using the individual healthy reference ranges for men aged <50, >50<60, >60<70 and those men >70 years of age).

Relationship between age and health indices age was significantly positively correlated with PSA levels in both groups (Active treatment group, r=0.250, p=0.01; Placebo group r=0.237, p=0.03). There was no correlation between age and severity of symptoms at any time point as measured by the IPSS in either group (Active treatment group, r=0.037, p=0.72; Placebo group r=0.048, p=0.64). There was no correlation between PSA levels and either total testosterone or free testosterone or oestradiol, cortisol, dehydroepiandrosterone (DHEA), sex hormone binding globulin (SHBG), or blood glucose in either group. Age was not correlated with total testosterone in either group however, free testosterone was negatively correlated with age in the active group (r=206, p=0.04) and placebo group (r=0.208, p=0.5). In both groups, at baseline, BMI positively correlated with both total testosterone levels (active treatment, r=0.429, p<0.01; placebo group, r=0.35, p<0.001).

There was no change in general health parameters; including weight or blood pressure during the study for either the active treatment or placebo group. There were no significant changes in lifestyle including sleep patterns, the type or duration of physical activity in either group.

There was no significant difference between the groups at baseline. The average IPSS score for active treatment and placebo groups respectively were 22.0 and 20.0, considered to be in "severely symptomatic". There was a gradual significant reduction in IPSS over time in the active treatment group from a score of 22.0 to 15.1, considered to be "moderately symptomatic". The IPSS score remained relatively stable at all time points in the placebo group. Repeated measures ANOVA showed a significant difference across time $F(1,406)=12.72$, $P<0.001$ and a significant difference between groups $F(1,1508)=47.23$, $P=0.001$ for total IPSS Score.

Figure 2:
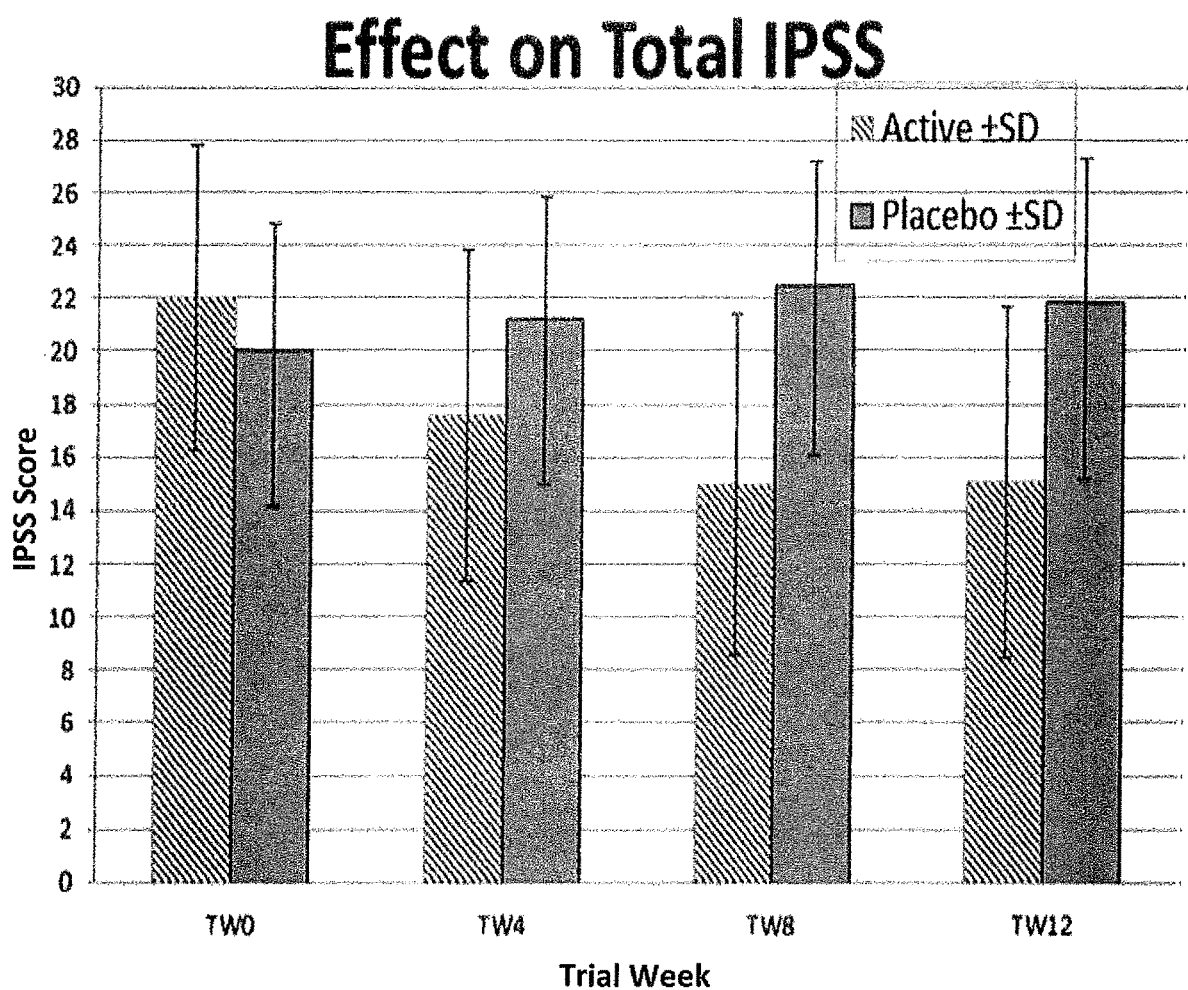
FIG. 2 depicts the results of International Prostate Symptom Score (IPSS) questionnaire assessments measured over 12 weeks after daily administration of *A. conyzoides* tablets (250 mg) in accordance with an embodiment of the of the present invention.

As shown in FIG. 2, in the Active treatment group, there was a steady reduction in the symptom severity for all questions in the IPSS at TW4 and then at TW8 and this effect was maintained at TW12. There were no changes observed in the average responses of the placebo group. The night time urinary frequency was reported in question seven; this reduced from 2.5-1.7 in the Active treatment group but remained relatively constant in the placebo group (2.2 to 2.4). At baseline, the average quality of life response (question eight) was four (Mostly unhappy about the condition) for both groups. There was a slight improvement in the Active treatment group who reported an average score of three (mixed feelings about the condition) after the treatment period.

Figure 3:
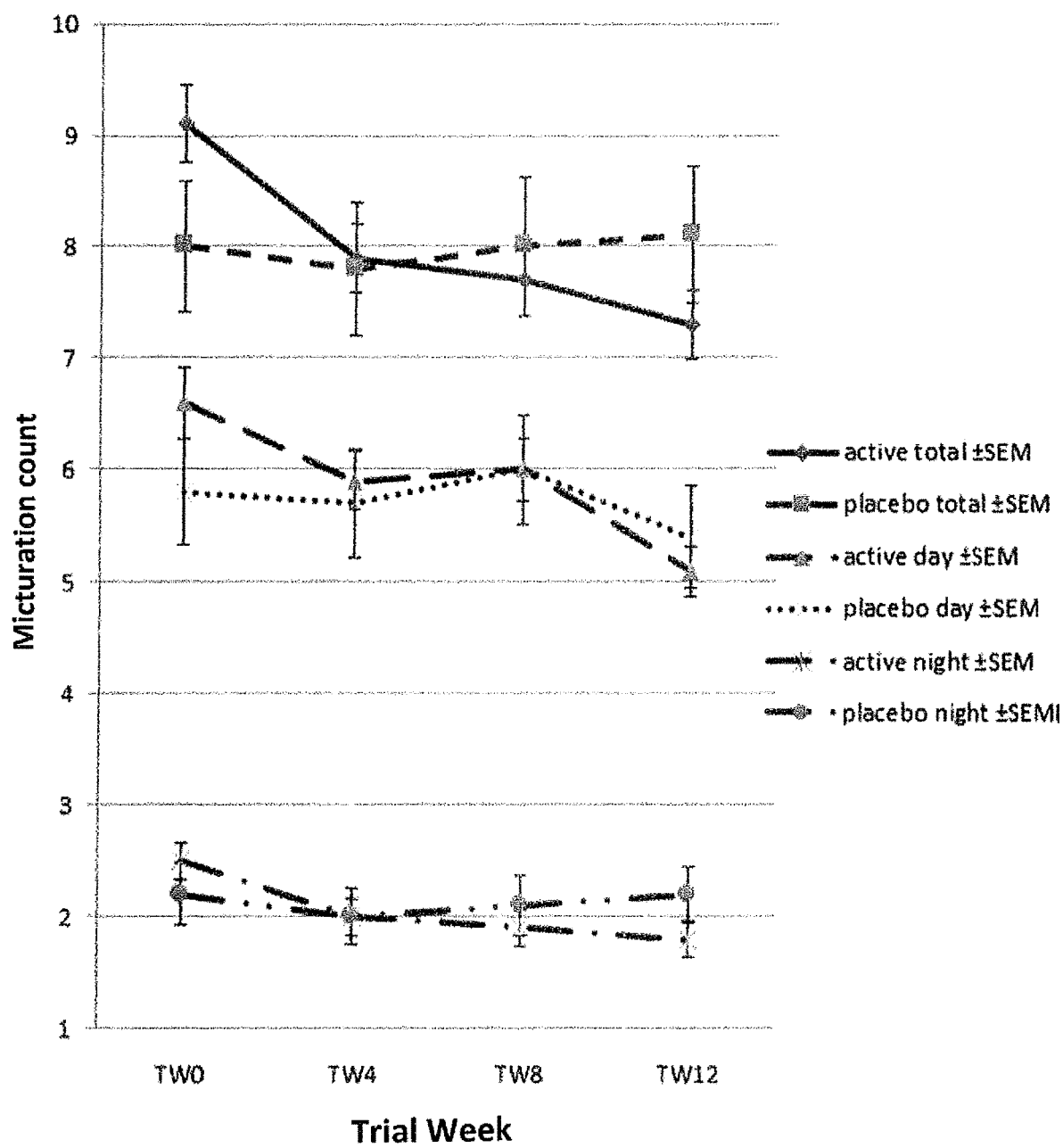
FIG. 3 illustrates the effect of *A. conyzoides* supplementation and placebo on Urinary Frequency in male human subjects at $Tw_0$, $Tw_4$, $Tw_5$, $Tw_{12}$. Active treatment is *A. conyzoides* extract 250 mg/d [results from participant-reported diary of day-time urinary frequency and night-time urinary frequency at $Tw_0$, $Tw_4$, $Tw_5$, $Tw_{12}$]. Significance at $P<0.05$; Wilcoxon rank sum test with continuity correction was used.

The average day-time and night-time urinary frequency for the active treatment and placebo treatment groups at TW0 were similar at baseline, and reflected a total daily urinary frequency of approximately nine times per day. For most people, normal frequency is about six to seven times in a 24-hour period. There was a steady decrease in both day-time frequency and night-time frequency in the active treatment group observed at TW4 and this continued at TW8 and TW12. The total frequency in the Active treatment group significantly reduced from 9.2 to 7.3 times per day over the treatment. There was no change in day-time or night-time urinary frequency in the placebo group. This resulted in a significant difference between groups for day-time frequency (W=1827, p-value=7.167e-06) and night-time frequency (W=1999, p-value=1.015e-08). See, FIG. 3.

The severity of the aging-related symptoms, often attributed to andropause and low testosterone, was assessed using the AMS questionnaire at TW0 and TW12. Both the active treatment and placebo groups had the same symptom severity at commencement of treatment. There was a no change in total AMS score or the psychological, somatic or sexual sub-domains in either the active treatment group or the placebo group at TW12, which is consistent with the no changes observed in total and free testosterone levels.

Effect on Hormones, Cholesterol, Triglycerides and PSA levels is discussed below. The androgens, total testosterone, free testosterone, androstenedione and dihydrotestosterone (DHT) as well as sex hormone binding globulin (SHBG) were in the healthy reference range for both groups and remained stable over the 12 weeks. There were no changes in cortisol or DHEA levels in either group. Total cholesterol and triglycerides remained stable over the treatment in both groups. The average PSA levels did not change in either Active treatment or placebo group after treatment.

The effect of *Ageratum conyzoides* on sexual function was assessed using the Derogatis Interview for Sexual Functioning-Self Report (DISF-SR) at baseline and at week 12 for those men that chose to answer the questionnaires. There was no significant change in the total score or the sub-domain scores in active treatment group after treatment. There were no changes observed in the placebo group before or after treatment in total score or any sub-domain. Taken together, these results are indicative of unaltered total and free testosterone.

DISCUSSION

The randomized placebo controlled clinical study demonstrated that the *A. conyzoides* extract significantly reduced the severity of BPH symptoms in otherwise healthy men, when administered for 12 weeks to those human male subjects. The clinical improvement was accompanied by significant reductions in both day- and night-time urinary frequency as well as an overall improvement in quality of life. The gene expression study indicated that *A. conyzoides* inhibits mRNA expression of DHT in human prostate epithelial cells and may have a similar mechanism of action as 5-alpha-reductase inhibitors for the management of symptoms of BPH.

Previous studies have been predominantly in vitro and lab animal experiments. The present human clinical study conducted a short-term safety evaluation of the *A. conyzoides* extract. In this study, there were no notable effects on hematological and biochemical parameters, lipids, or blood glucose levels at the administered dose of 250 mg/d of *A. conyzoides* extract over 12 weeks. Research has shown that significant suppression of DHT by pharmaceutical 5-alpha-reductase inhibitors may cause exacerbation of symptoms of low testosterone, similar to that in young men with hypogonadism, such as reduced sexual function and may increase the risk of hypoactive sexual desire. The administration of *A. conyzoides* extract did not suppress testosterone or DHT levels in this short-term study. Furthermore, there were no changes in sexual functioning (using the DISF-SR) or aging male symptoms (as assessed by the AMS), which are linked to low androgen status in older men. Furthermore, the PSA levels did not correlate with severity of BPH symptoms, as assessed by the IPPS in this cohort. These results support previous research that age itself has a greater influence on prostate health than does androgen status in otherwise healthy aging men.

The men in this study were not experiencing anxiety and/or depressive symptoms and the levels of the hormones cortisol and DHEA-S were in the healthy reference range and stayed stable throughout the study. It is noteworthy that depression and anxiety may influence the clinical manifestation of BPH with anxious patients having a lower response to treatment.

Although the two main factors that trigger BPH are commonly reported as being aging and high androgen levels, inflammation is likely to be another factor in the development of BPH (Sciarra, A., et al., "Prostate growth and inflammation," *J. Steroid Biochem. Mol. Biol.* (2008) 108:254-260). Chronic inflammation can lead to repeated tissue damage resulting in cellular proliferation, which could predispose a human subject to hyperplastic growth (Robert, G., et al., "Inflammation in benign prostatic hyperplasia: a 282 patients' immunohistochemical analysis," *Prostate* (2009) 69:1774-1780). It is likely that the efficacy of *A. conyzoides* extract in reducing symptoms of BPH in the present study is also due to anti-inflammatory and antispasmotic action of the tested composition.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

We claim:

1. A method for treating symptoms associated with benign prostatic hyperplasia in a human male subject, comprising the steps of administering to the subject in need of such treatment an effective amount of a composition comprising an extract of *Ageratum* spp. wherein the symptoms are decreased.

2. The method according to claim 1, wherein the *Ageratum* spp. is selected from the group consisting of *Ageratum conyzoides*, *Ageratum coeruleum*, and *Ageratum houstonianum*.

3. The method according to claim 1, further wherein the composition is effective to inhibit 5-alpha-reductase type 2 activity.

4. The method according to claim 3, wherein the *Ageratum* spp. is *Ageratum conyzoides*.

5. The method according to claim 1, wherein the *Ageratum* spp. is *Ageratum conyzoides*, and further wherein the effective amount of *Ageratum conyzoides* extract for a total daily dose is in a range from about 50 mg to about 500 mg.

6. The method according to claim 1, wherein the *Ageratum* spp. is *Ageratum conyzoides*, and further wherein the effective amount of *Ageratum conyzoides* extract for a total daily dose is about 250 mg.

7. The method according to claim 1, wherein the *Ageratum* spp. is *Ageratum conyzoides*, and further wherein the effective amount of *Ageratum conyzoides* extract for a total daily dose is about 2.5 mg/kg to about 3.5 mg/kg.

8. The method according to claim 1, wherein the symptoms are selected from the group consisting of urinary frequency, urinary urgency, inflammation, urinary tract obstruction, and urinary tract infection.

9. A method for treatment of urinary symptoms associated with benign prostatic hyperplasia in a human male subject, comprising administering to the subject in need of such treatment an effective amount of a composition comprising *Ageratum* spp. extract wherein the urinary symptoms are decreased.

10. The method according to claim 9, wherein the *Ageratum* spp. is selected from the group consisting of *Ageratum conyzoides*, *Ageratum coeruleum*, and *Ageratum houstonianum*.

11. The method according to claim 9, further wherein the composition is effective to inhibit 5-alpha-reductase type 2 activity.

12. The method according to claim 11, wherein the *Ageratum* spp. is *Ageratum conyzoides*.

13. The method according to claim 9, wherein the *Ageratum* spp. is *Ageratum conyzoides*, and further wherein the effective amount of *Ageratum conyzoides* extract for a total daily dose is in a range from about 50 mg to about 500 mg.

14. The method according to claim 9, wherein the *Ageratum* spp. is *Ageratum conyzoides*, and further wherein the effective amount of *Ageratum conyzoides* extract for a total daily dose is about 250 mg.

15. The method according to claim 14, wherein the urinary symptom is daily urinary frequency.

16. The method according to claim 15, wherein daily urinary frequency is decreased by about 2 times per day.

17. The method according to claim 16, wherein the composition is administered over about 12 weeks.

18. The method of claim 1, wherein the composition consists essentially of an extract of *Ageratum* spp.

19. The method of claim 1, wherein the composition consists of an extract of *Ageratum* spp.

* * * * *